United States Patent
Yanagi et al.

(10) Patent No.: US 10,761,057 B2
(45) Date of Patent: Sep. 1, 2020

(54) MEMBRANE DEVICE AND METHOD FOR MANUFACTURING SAME

(71) Applicant: Hitachi, Ltd., Tokyo (JP)

(72) Inventors: Itaru Yanagi, Tokyo (JP); Kenichi Takeda, Tokyo (JP)

(73) Assignee: HITACHI, LTD., Tokyo (JP)

(*) Notice: Subject to any disclaimer, the term of this patent is extended or adjusted under 35 U.S.C. 154(b) by 321 days.

(21) Appl. No.: 15/545,431

(22) PCT Filed: Feb. 13, 2015

(86) PCT No.: PCT/JP2015/054002
§ 371 (c)(1),
(2) Date: Jul. 21, 2017

(87) PCT Pub. No.: WO2016/129111
PCT Pub. Date: Aug. 18, 2016

(65) Prior Publication Data
US 2018/0003673 A1 Jan. 4, 2018

(51) Int. Cl.
*G01N 27/447* (2006.01)
*C23C 16/34* (2006.01)
(Continued)

(52) U.S. Cl.
CPC ....... *G01N 27/44791* (2013.01); *C23C 16/24* (2013.01); *C23C 16/345* (2013.01); *G01N 33/48721* (2013.01); *G01N 27/447* (2013.01)

(58) Field of Classification Search
CPC ....... B82Y 5/00; B82Y 40/00; Y10S 977/888; Y10S 977/89; Y10S 977/924
See application file for complete search history.

(56) References Cited

U.S. PATENT DOCUMENTS 10,338,057 B2 * 7/2019 Yanagi ............. G01N 27/44791
10,416,147 B2 * 9/2019 Yanagi ............. G01N 33/48721
(Continued)

FOREIGN PATENT DOCUMENTS

JP 2002-090219 A 3/2002
JP 2006-108491 A 4/2006
JP 2012-040619 A 3/2012

OTHER PUBLICATIONS

Seidel et al, Anisotropic Etching of Crystalline Silicon in Alkaline Solutions, J. Electrochem. Soc., vol. 137, No. 11, Nov. 1990, pp. 3626-3632 (Year: 1990).*
(Continued)

*Primary Examiner* — Hoa (Holly) Le
(74) *Attorney, Agent, or Firm* — Mattingly & Malur, PC

(57) ABSTRACT

A method for producing a membrane device includes: forming an insulating film as a first film on a Si substrate; forming a Si film as a second film on the entire surface or a part of the first film; forming an insulating film as a third film on the second film; forming an aperture so as to pass through a part of the third film positioned on the second film and not to pass through the second film; etching a part of the substrate on one side of the first film with a solution that does not etch the first film; and etching a part or all of the second film on the other side of the first film with a gas or a solution that does not etch the first film and has an etching rate for the third film lower than an etching rate for the second film.

15 Claims, 17 Drawing Sheets

(51) Int. Cl.
*G01N 33/487* (2006.01)
*C23C 16/24* (2006.01)

(56) References Cited

U.S. PATENT DOCUMENTS

| | | | |
|---|---|---|---|
| 2013/0092541 A1 | 4/2013 | Drndic et al. | |
| 2017/0307587 A1* | 10/2017 | Yanagi | G01N 27/3278 |
| 2019/0004030 A1* | 1/2019 | Yanagi | B81C 1/00158 |
| 2019/0094180 A1* | 3/2019 | Yanagi | G01N 21/6486 |

OTHER PUBLICATIONS

Khan et al, Fabrication of Solid State Nanopore in Thin Silicon Membrane Using Low Cost Multistep Chemical Etching, Materials (Basel). Nov. 2015; 8(11): 7389-7400. (Year: 2015).*
Shah et al., Absolute etch rates in alkaline etching of silicon (111), Sensors and Actuators A164 (2010) 154-160 (Year: 2010).*
DesOrmeaux et al., Nanoporous silicon nitride membranes fabricated from porous nanocrystalline silicon templates, the Royal Society of Chemistry 2014; DOI: 10.1039/c4nr03070b (Year: 2014).*
Itaru Yanagi, et al., "Fabricating nanopores with diameters of sub-1 nm to 3 nm using multilevel pulse-voltage injection", Scientific Report 4, 5000; DOI: 10.1038/srep 05000, May 21, 2014.
Venta, et al., "Differentiation of short, single-stranded DNA homopolymers in solid-state nanopores" ACS Nano vol. 7, No. 5, 2013, pp. 4629-4636.
International Search Report of PCT/JP2015/054002 dated May 19, 2015.

* cited by examiner

[FIG. 1]
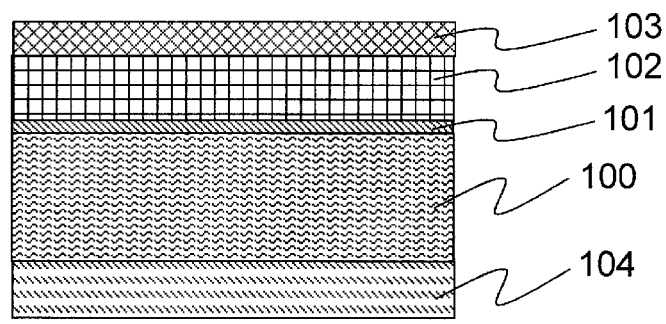
[FIG. 2]
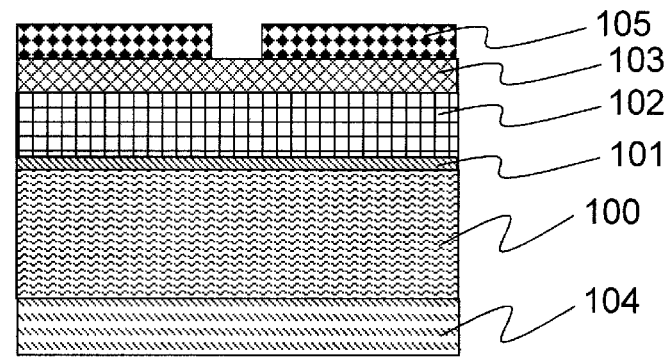
[FIG. 3]
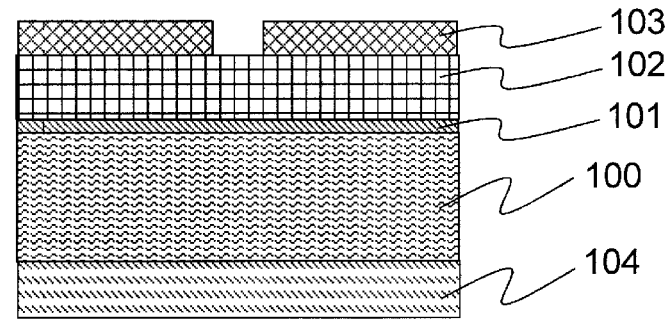

[FIG. 4]
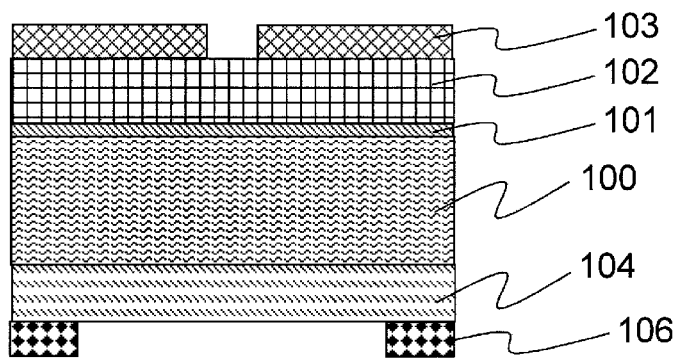
[FIG. 5]
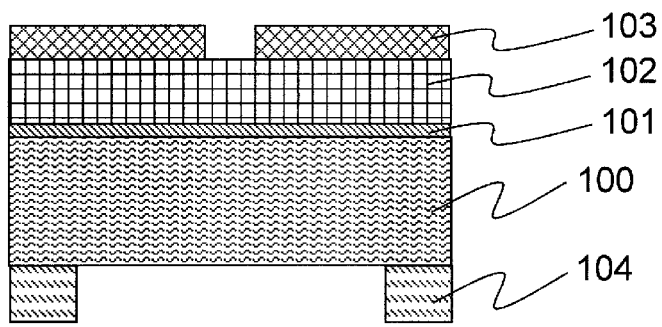
[FIG. 6]
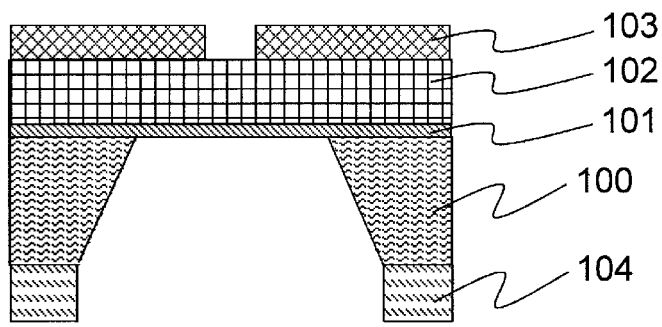

[FIG. 7]
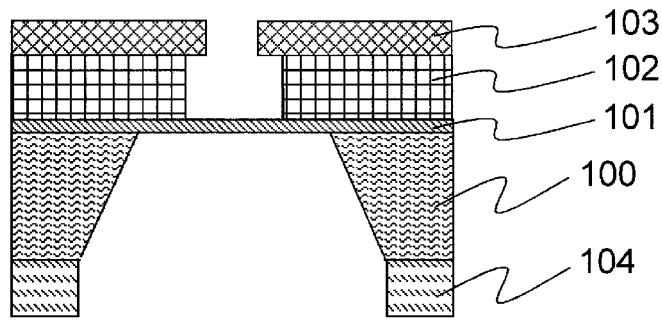
[FIG. 8]
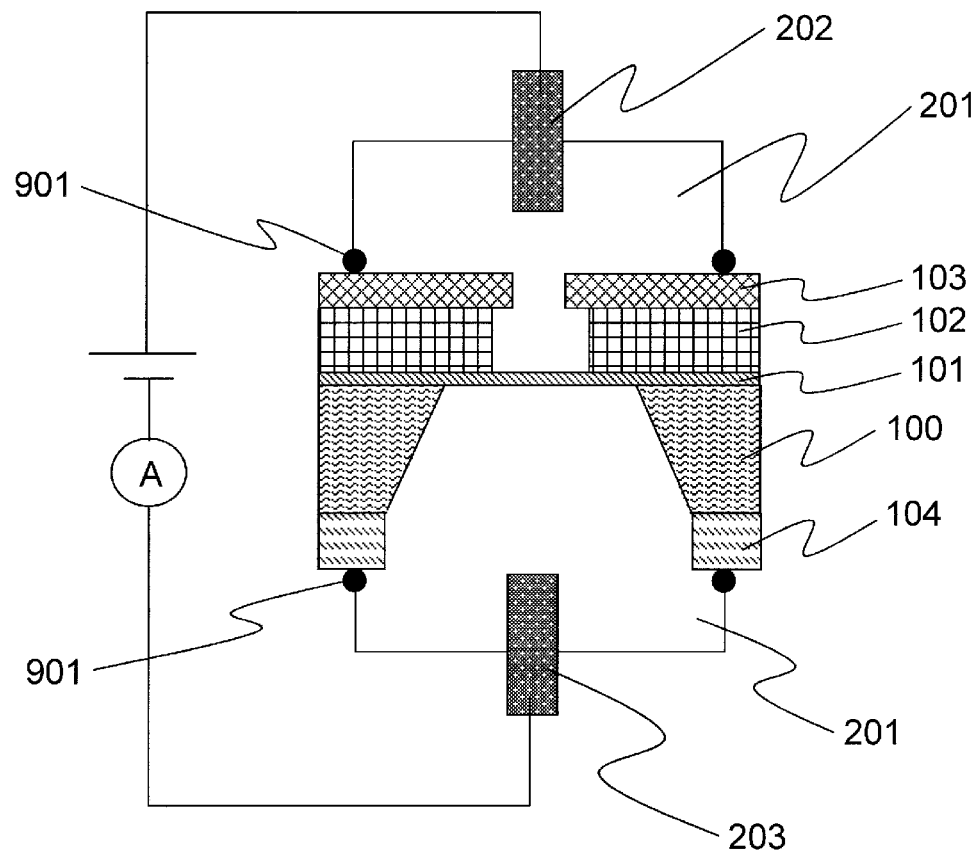

[FIG. 9]
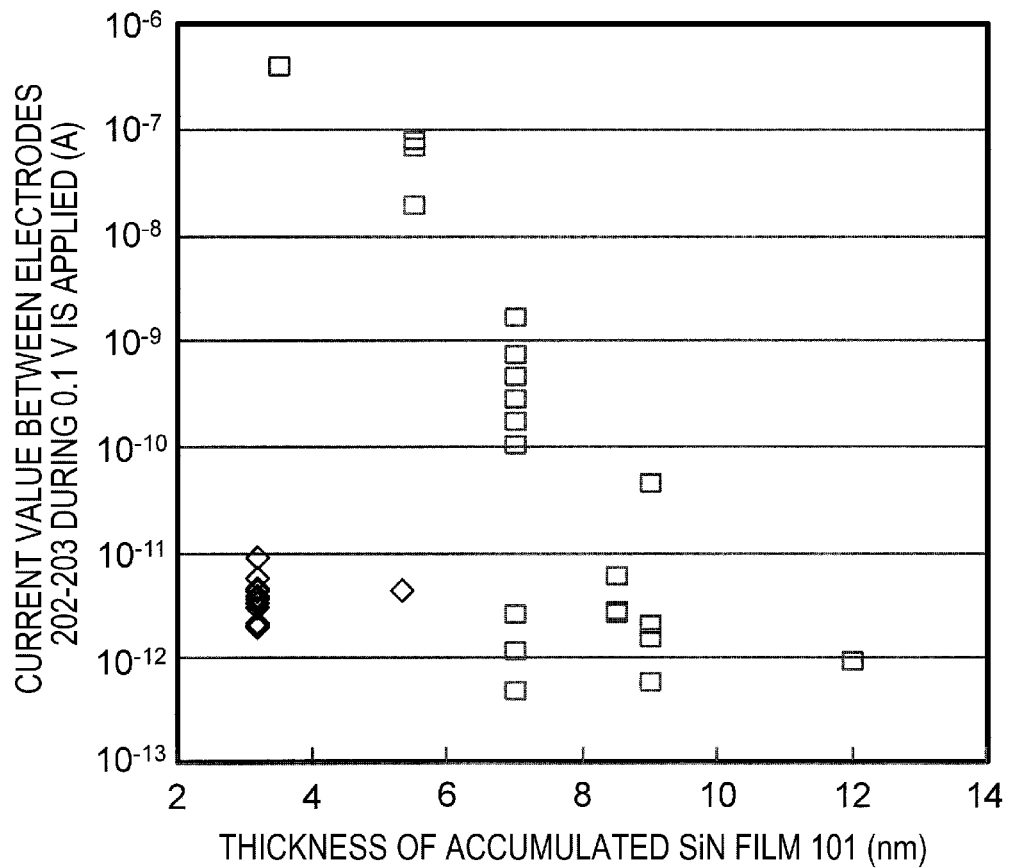
□ : COMPARATIVE EXAMPLES
◇ : EXAMPLES
[FIG. 10]
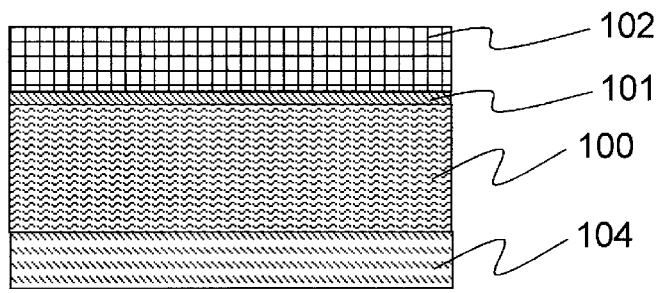

[FIG. 11]
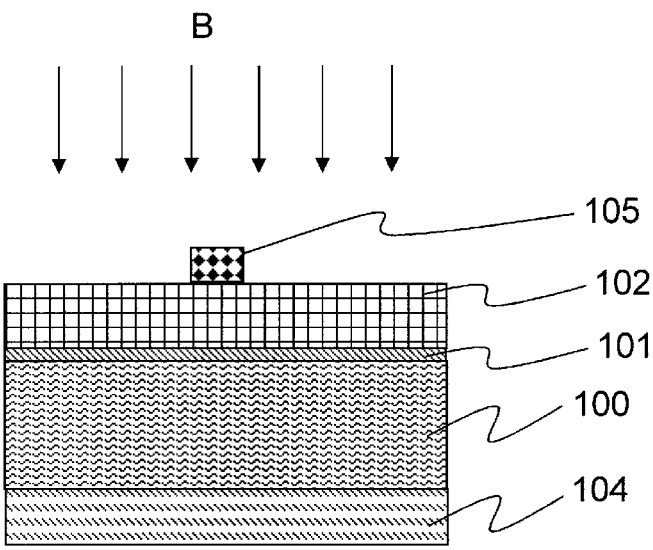
[FIG. 12]
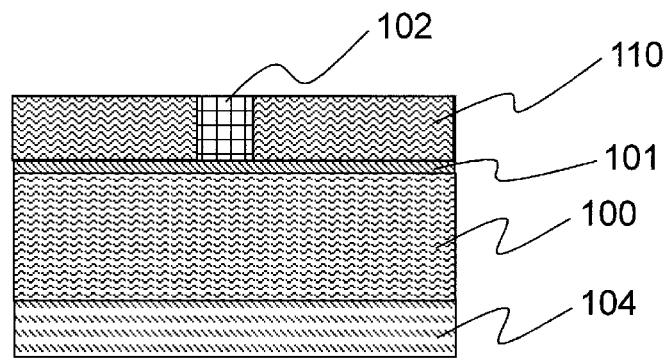
[FIG. 13]
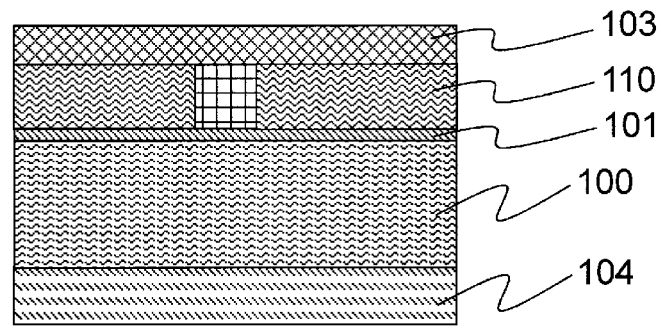

[FIG. 14]
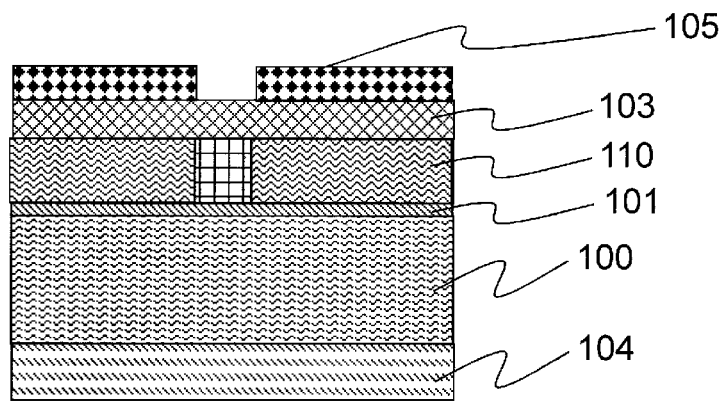
[FIG. 15]
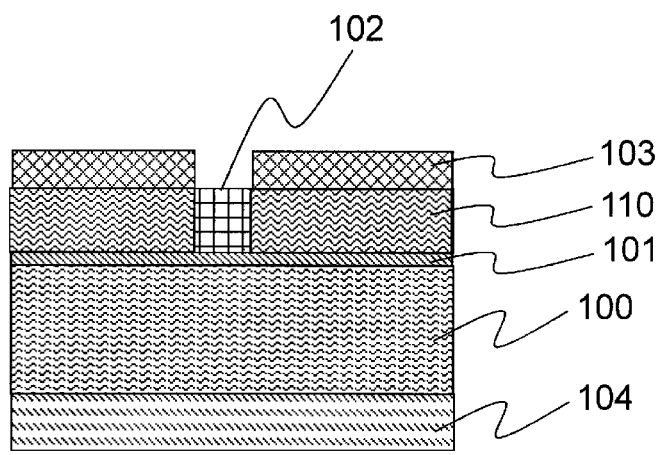

[FIG. 16]
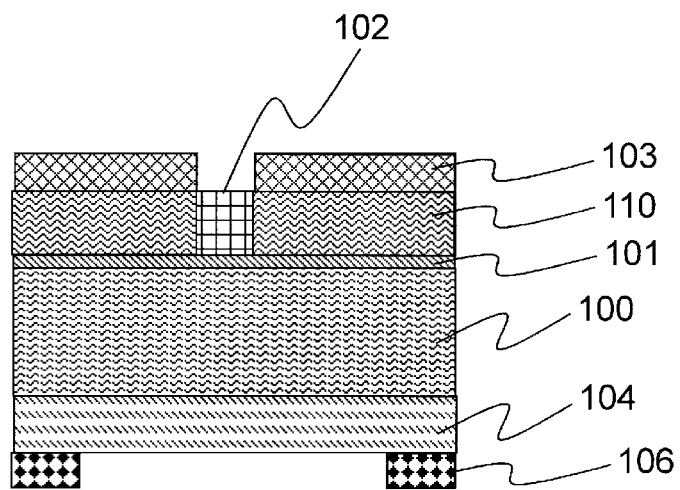
[FIG. 17]
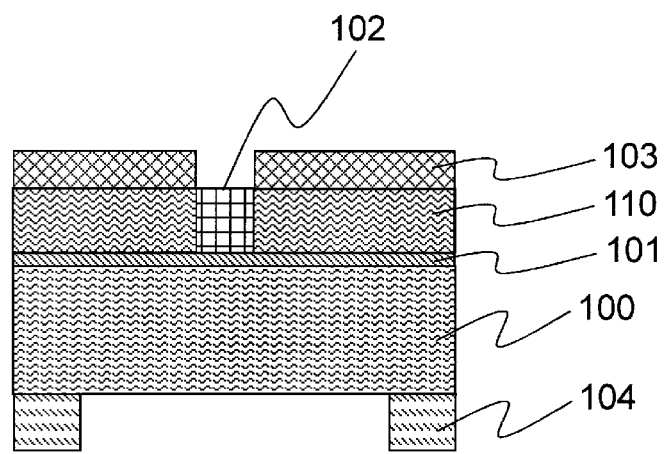

[FIG. 18]
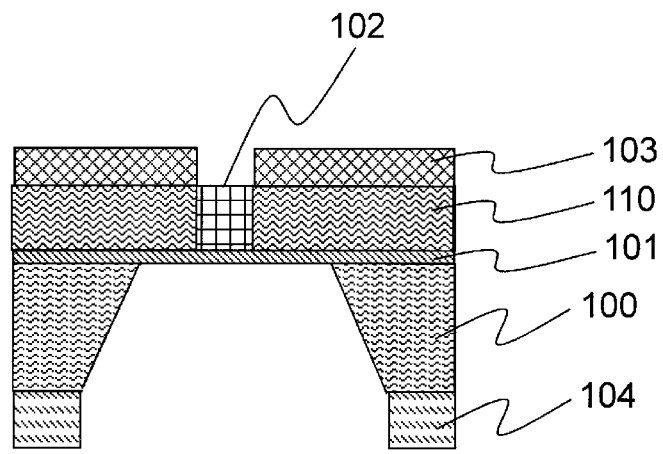
[FIG. 19]
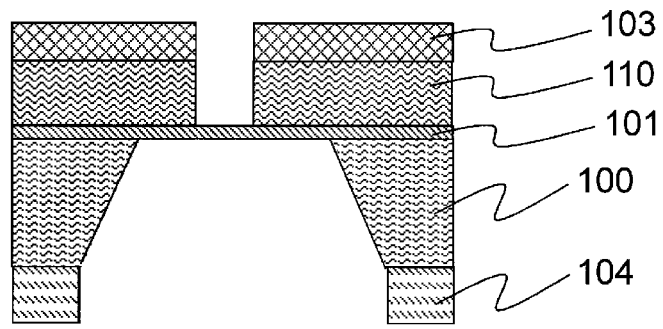
[FIG. 20]
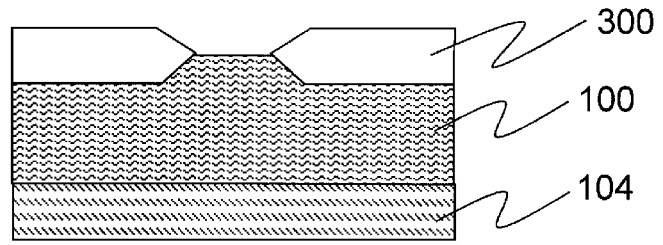

[FIG. 21]
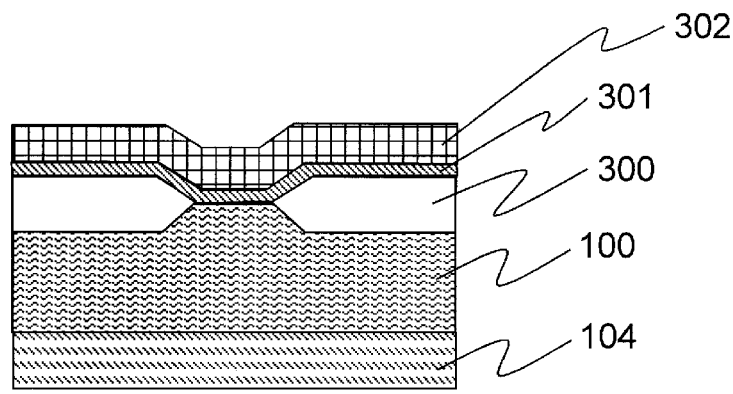
[FIG. 22]
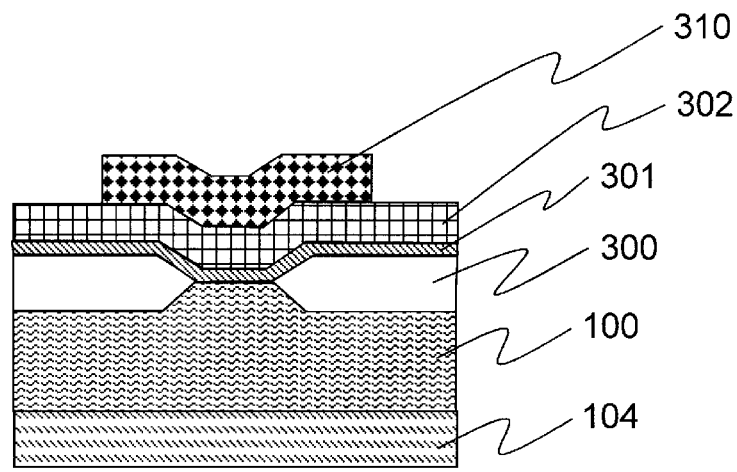
[FIG. 23]
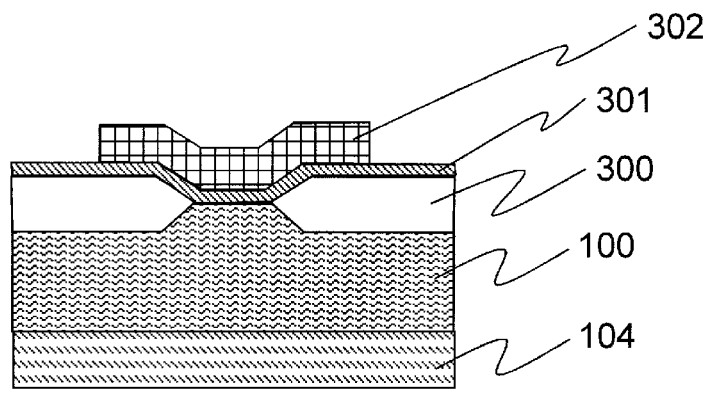

[FIG. 24]
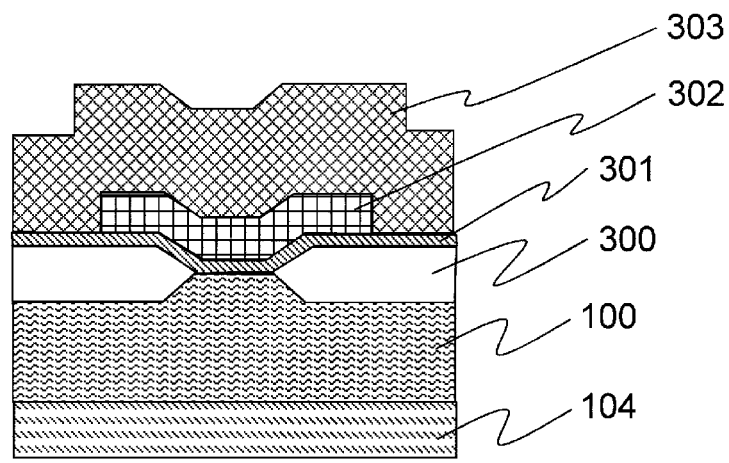
[FIG. 25]
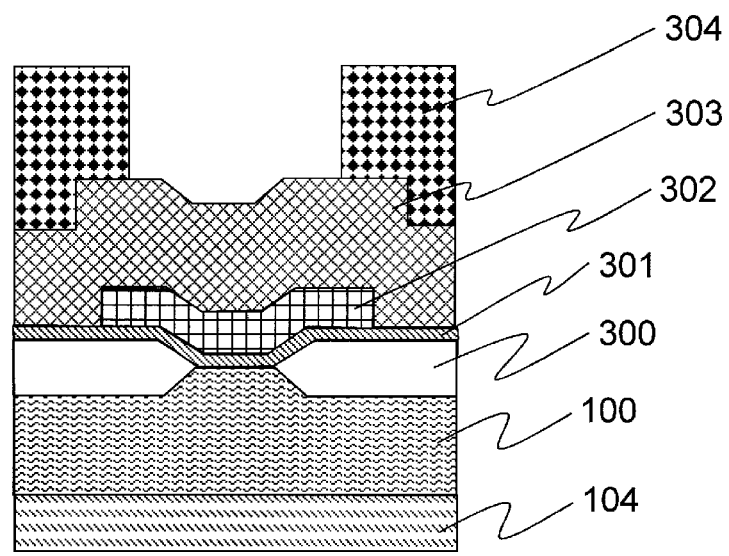

[FIG. 26]
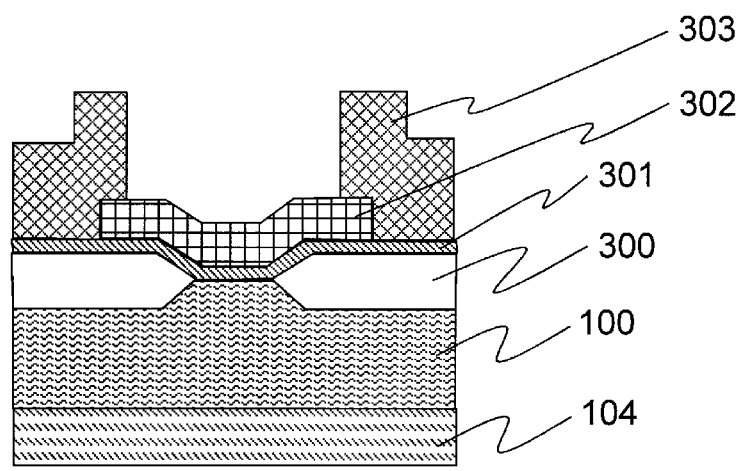
[FIG. 27]
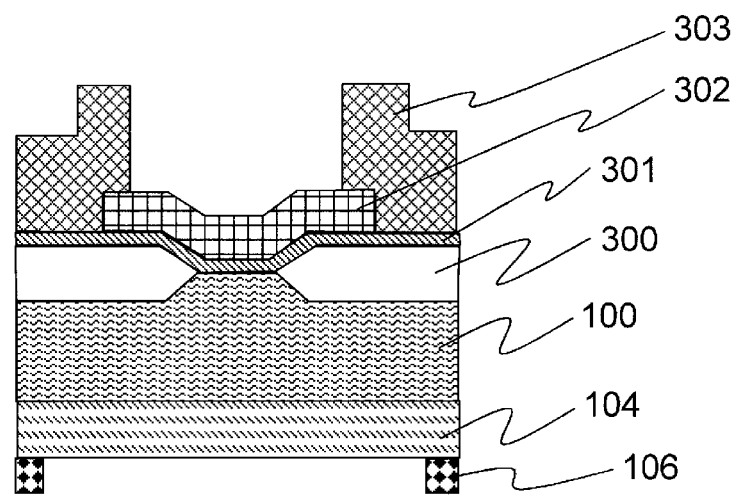

[FIG. 28]
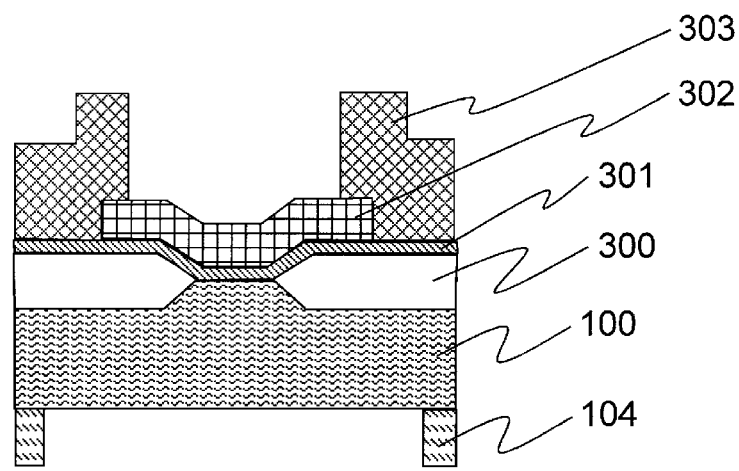
[FIG. 29]
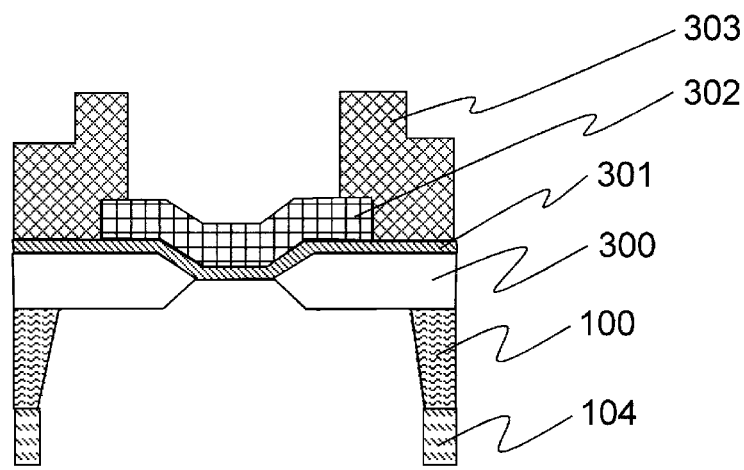

[FIG. 30]
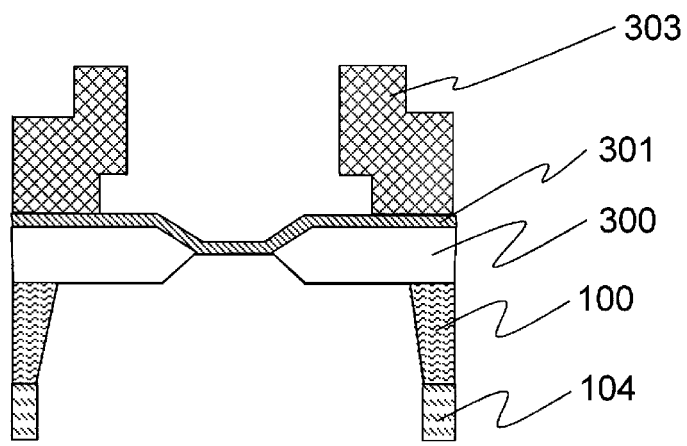
[FIG. 31]
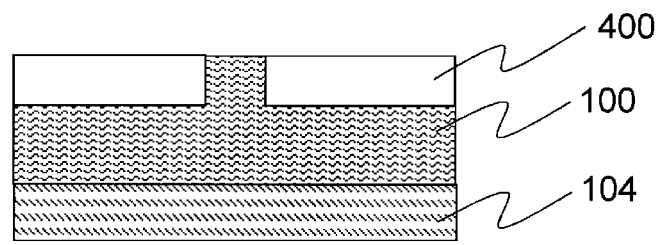
[FIG. 32]
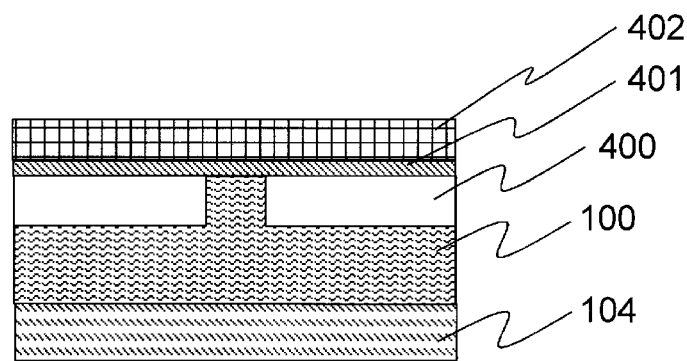

[FIG. 33]
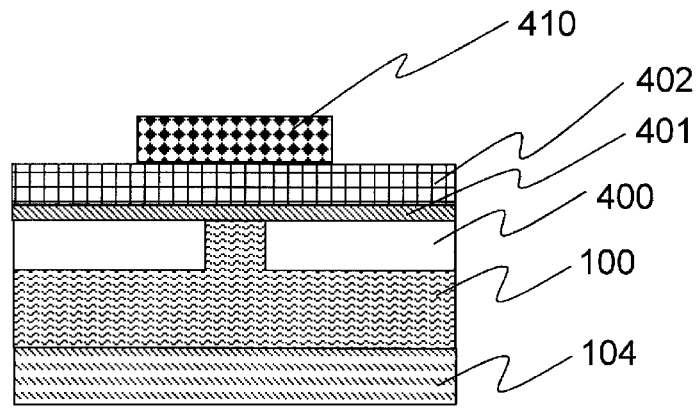
[FIG. 34]
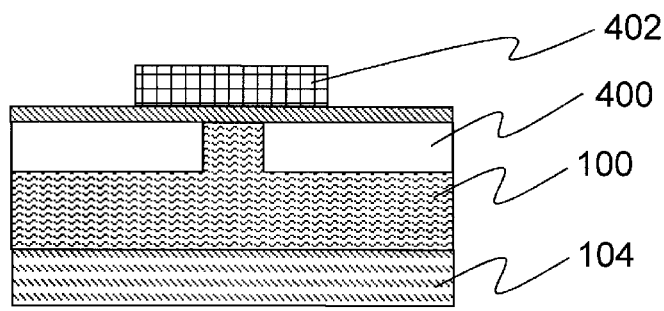
[FIG. 35]
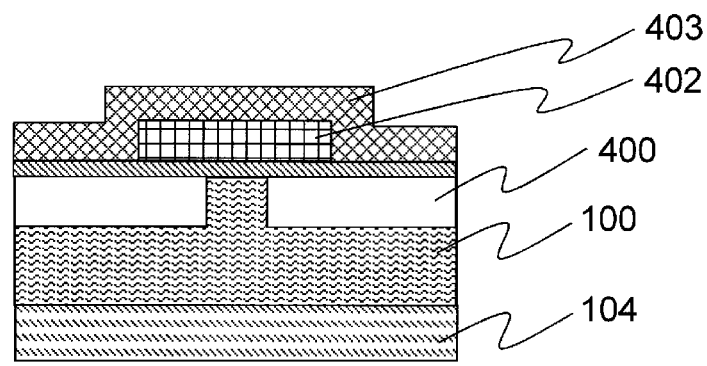

[FIG. 36]
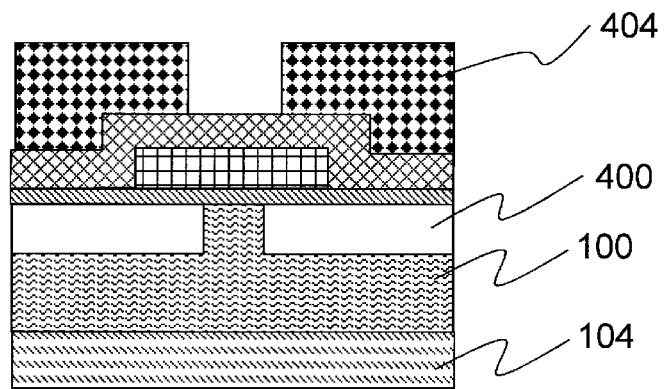
[FIG. 37]
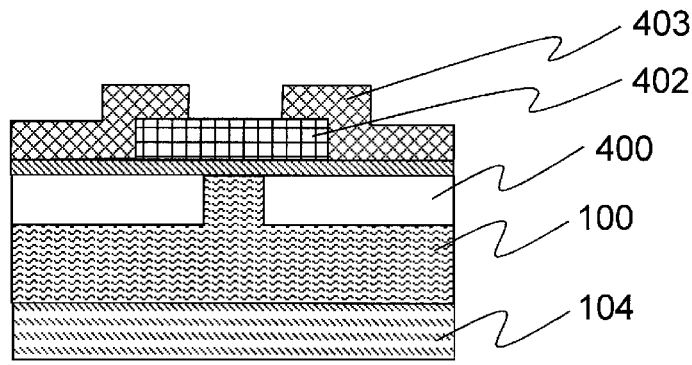
[FIG. 38]
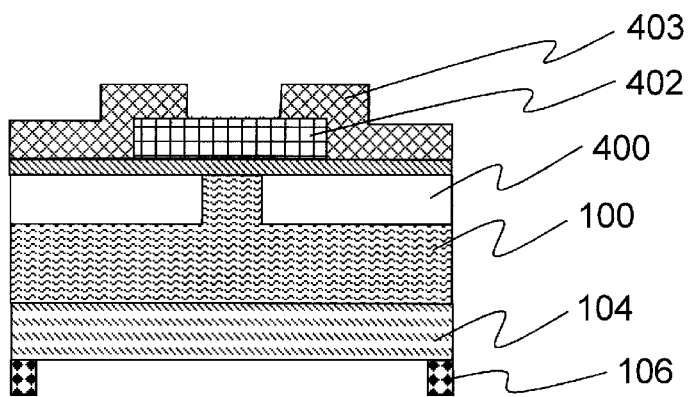

[FIG. 39]
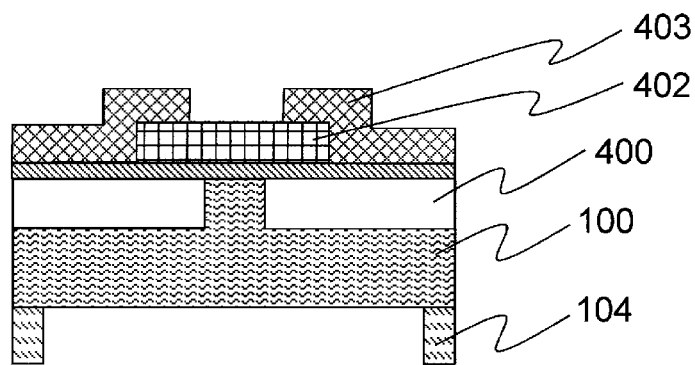
[FIG. 40]
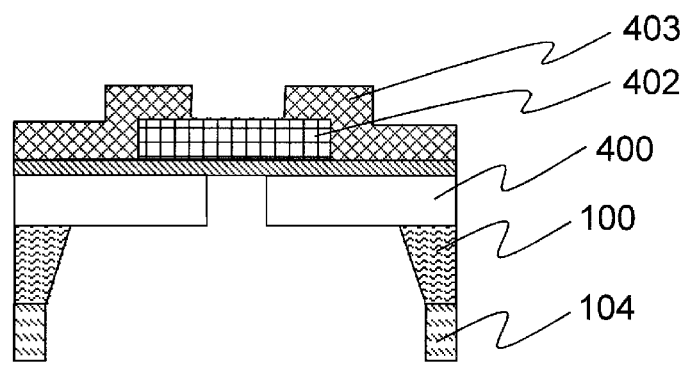
[FIG. 41]
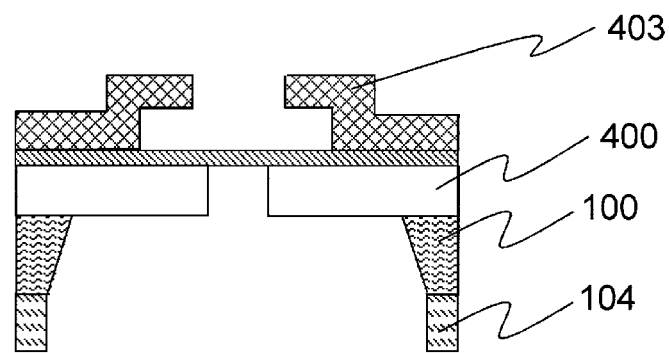

[FIG. 42]
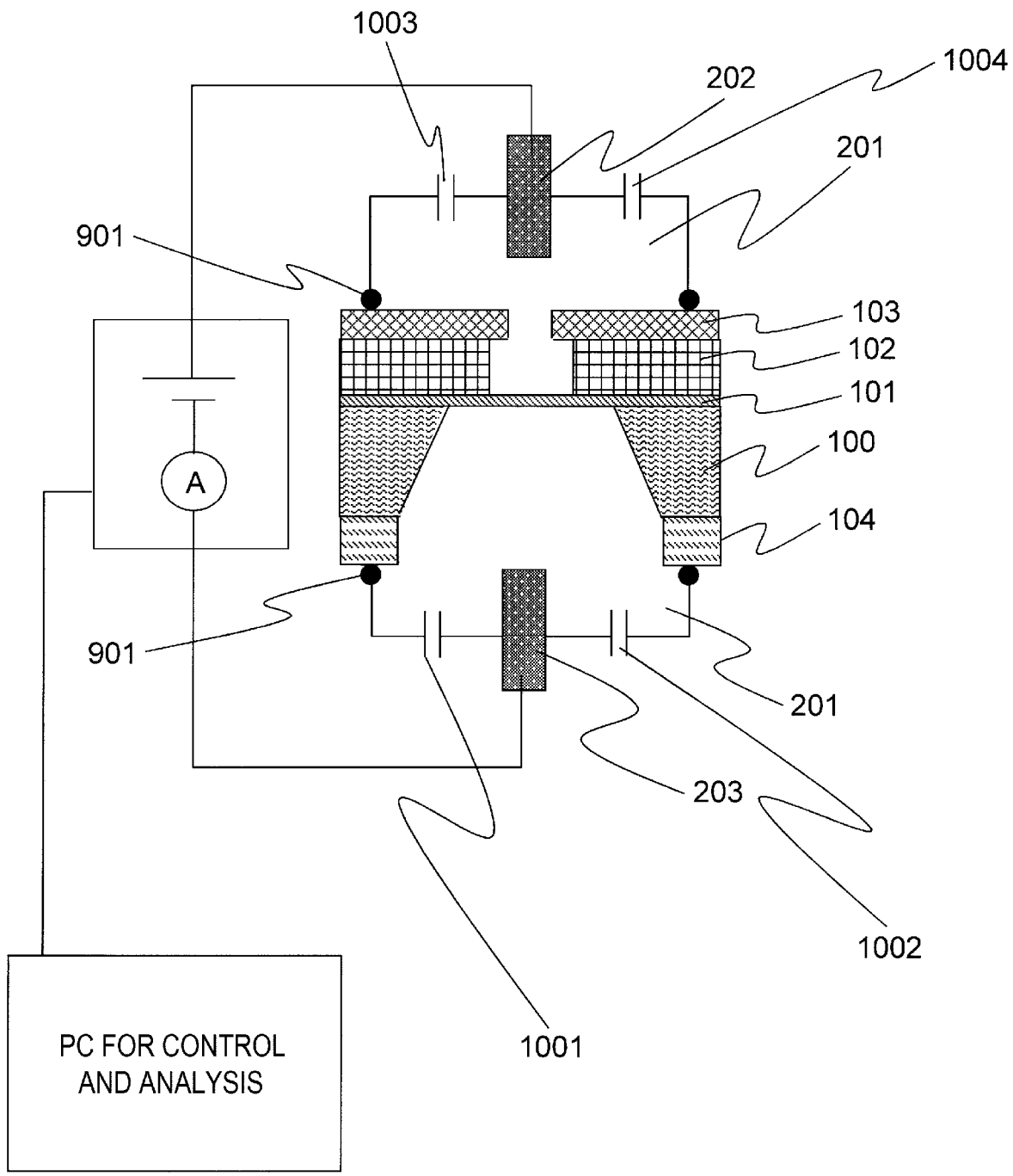

MEMBRANE DEVICE AND METHOD FOR MANUFACTURING SAME

TECHNICAL FIELD

The present invention discloses techniques regarding a thin film membrane device and a formation of a membrane, for use in, for example, a detection device.

BACKGROUND ART

As an approach for realizing a more advanced generation DNA sequencer, techniques using nanopores have been studied. That is, an aperture (nanopore) having a size similar to DNA are provided in a thin film membrane, an upper and lower chambers of the thin film membrane are filled with an aqueous solution, electrodes are provided in the two chambers so as to be in contact with the aqueous solution, DNA to be measured is put in one of the chambers, a potential difference is caused between the electrodes provided in the two chambers to subject the DNA to electrophoresis to allow the DNA to pass through the nanopore, and during this time, the temporal change in the ionic current flowing between the two electrodes is measured, thereby determining a structural feature or the basic sequence of the DNA. The above technique is useful for acquiring a structural feature of not only DNA but also various biological molecules.

For producing the nanopore device, methods using a semiconductor substrate, a semiconductor material, or a semiconductor process, which has a high mechanical strength or other characteristics, are attracting attentions. For example, a thin film membrane can be formed with a silicon nitride film (SiN film). Voltage stress is applied to a membrane in an ionic aqueous solution to cause dielectric breakdown, whereby fine pinholes can be bored to form a nanopore in the membrane (NPL 1). In an alternative method, a nanopore can be formed by subjecting a membrane to etching by a focused electron ray.

One of important factors for determining accuracy in DNA reading by a nanopore sequencer is a film thickness of the membrane. Specifically, a smaller thickness of the membrane is more preferred. The reason is that the interval between adjacent two of four kinds of bases arranged in a DNA strand is approximately 0.34 nm, and the larger the thickness of the membrane is as compared to the interval, the larger number of bases are simultaneously placed in one nanopore. In this situation, a signal obtained by measuring a current is a signal generated by multiple bases, resulting in reduction of the accuracy of base sequence determination and leading to a complicated signal analysis. Also when acquisition of structural features is intended for various biological molecules other than DNA, a larger thickness of the membrane results in reduction of space resolution. Accordingly, for enhancement of accuracy in structure determination of a substance to be measured, it is highly important to make the thickness of the membrane having a nanopore as small as possible.

In order to reduce the thickness of a membrane, it is obviously preferred that the membrane area is as small as possible. The smaller the membrane area, the lower the possibility of presence of unavoidable defects (weak spots or pinholes due to bonding failure between atoms) generated during forming the membrane in the membrane. In addition, when the membrane is formed, it is important to avoid a process involving the possibility of scratching and breaking the membrane as much as possible.

Hereinunder, attempts of reduction in thickness of a membrane will be described with explanation of some examples of a conventional representative method for forming a membrane using a semiconductor material.

In the simplest method of forming a membrane, a film of a material for the membrane (e.g., SiN) is formed on a Si substrate, a film of SiN is formed on the back surface, a part of the SiN film on the back surface is etched so as to expose the Si substrate, and then the Si substrate is etched with an aqueous solution of KOH or TMAH from the part of the back surface where the Si is exposed, toward the front surface, whereby a membrane supported on the Si substrate can be formed. In this method, it is difficult to make the area of the membrane small. Although the etching of the Si substrate with the KOH aqueous solution or TMAH aqueous solution is a crystal anisotropy etching in which only the (100) face is preferentially etched, etchings in other directions than the (100) face proceeds in certain degrees and variation in etching shape is also large. In particular, etching proceeds also in an unexpected direction with a crystal defect present in Si as the starting point, and therefore the variation in shape increases. In addition, the thickness of the Si substrate to be etched is generally large and at least 100 um or more (for example, 725 um in the case of a Si wafer of 8 inches). The thickness of the substrate varies in one wafer or among wafers, and generally, there is a variation of 1 um or more. Thus, a membrane having a size greatly deviated from the membrane size expected from the shape of a mask of the SiN film on the back surface is formed. For the above reason, according to the result of our previous study, it has been difficult to stably form a membrane having an area of 50 um×50 um square or smaller size by this production method. However, in order to aim at forming a thin film membrane, it is required to make the area of the membrane further smaller.

In another production method, as described in NPL 1, a SiN film is formed on a Si substrate, then a $SiO_2$ film is formed on the SiN film, then SiN films are formed on the $SiO_2$ and the back surface of the Si substrate, then a part of the uppermost SiN film on the front surface side of the wafer is patterned by dry-etching to expose the $SiO_2$ film under the SiN film, then a part of the SiN film on the back surface is etched so as to expose the Si substrate, the Si substrate is etched from the back surface with a TMAH aqueous solution, then remove the $SiO_2$ film on the SiN film with an HF aqueous solution, whereby a SiN membrane can be formed. According to this method, if a hole pattern of, for example, 100 nm square or smaller is formed by using a latest lithography technique and dry etching in the patterning of the SiN on the $SiO_2$, after the subsequent $SiO_2$ etching with the HF aqueous solution, the thinnest area of the membrane (an area with a single layer of the SiN membrane) can be made into a size of approximately 100 to 500 nm square inclusive of the variation. In this respect, the method is advantageous in reduction of the membrane thickness.

However, an HF aqueous solution etches a SiN film although the etching rate is lower as compared with the case of a SiO2 film. For this reason, the contact of the HF aqueous solution with the SiN membrane of the thin film part causes breaking of the membrane. In the results of our experiments, the lower limit of the thickness of the membrane in the thinnest part is 7 nm in the above method.

In another method, as described in NPL 2, a thick SiN membrane is formed, and the thickness is reduced by dry etching in a partial area thereof. According to this method, since the thickness of the membrane can be reduced only in an area of a limited part by a latest lithography technique and dry etching, it is possible to achieve the surface area reduction in a thin film membrane part. However, variation in the dry etching rate among different batches is large, and the variation in the etching rate in one wafer surface is also large. Furthermore, since the SiN film before etching has a large thickness, variation in the initial film thickness is also large. For this reason, the thickness of the obtained membrane has large variations among different batches and different samples, relative to the target thickness. In dry etching, ions with a high energy collide with the membrane and therefore damage the membrane. In an ultrathin film area, therefore, there is a possibility of breaking the membrane, and hence the method is unsuitable to reduction of the membrane thickness. According to the description in NPL 2, the thickness of the SiN film is 5 to 8 nm.

Incidentally, a material that is used most widely as a membrane material is SiN. SiN has a high density, is hydrophilic, and is highly excellent in chemical stability. These give a great advantage for a nonopore sensor used in an aqueous solution. In fact, there are many studies in which a nanopore was formed in a SiN membrane and DNA passing through the nanopore was confirmed, other than NPL 1 and NPL 2, and a highly stable passing of DNA through a nanopore was confirmed. Thus, SiN is one of materials that are currently used most frequently as a membrane material for a nanopore sensor. In addition, SiN is excellent in mechanical strength and the membrane is difficult to break. SiN is one of the most general materials that are used in a semiconductor process, and is advantageous also in a very high compatibility with a conventional semiconductor process (for example, CMOS process). That is, a membrane of SiN can be produced in most semiconductor lines in the world. For this reason, a sensor (nanopore sensor) with a SiN membrane is expected to be spread to the industry without any large barrier. Even in the case where an MOS transistor circuit for measurement is installed on the same circuit board with a nanopore sensor, the membrane made of a SiN material is not a large barrier. For the above reasons, SiN is being greatly expected as a material of a nanopore membrane having a very small thickness.

CITATION LIST

Non-Patent Literature

NPL 1: Yanagi, I., Akahori, R., Hatano, T. & Takeda, K. "Fabricating nanopores with diameters of sub-1 nm to 3 nm using multilevel pulse-voltage injection" Sci. Rep. 4, 5000; DOI: 10.1038/srep 05000 (2014).

NPL 2: Venta, K. et al. "Differentiation of short, single-stranded DNA homopolymers in solid-state nanopores" ACS Nano 7, 4629-4636 (2013).

SUMMARY OF INVENTION

Technical Problem

As described in Background Art, for enhancing accuracy indetermination of a DNA base sequence, it is highly effective to make the thickness of a membrane in a nanopore sensor as small as possible. The thickness reduction is highly important for enhancing accuracy in structure determination of not only DNA but also other objects to be measured. Also, use of SiN as a membrane material in forming and using a nanopore sensor is highly advantageous as described in Background Art.

A thickness of a SiN membrane of 5 to 8 nm described in NPL 2 has been the smallest thickness of the conventionally-reported thicknesses of SiN membranes. Since the interval between adjacent two of four kinds of bases arranged in a DNA strand is less than 5 nm, needless to say, further reduction in thickness of the membrane to 5 nm or smaller leads to enhancement of the accuracy of DNA base sequence determination. Needless to say, also for enhancing accuracy of structure determination of other object to be measured than DNA, it is highly important to reduce the membrane thickness to further less than 5 nm.

Thus, the present invention shows a method for forming a SiN membrane having a thickness of 5 nm or less which thickness has not been achieved in conventional reports (known examples). In addition, the invention shows a method for forming a membrane of 5 nm or less in which a membrane can be formed with other materials than SiN using a semiconductor process.

Solution to Problem

A method for producing a membrane device which is an aspect of the present invention, includes: forming an insulating film as a first film on a Si substrate as a substrate; forming a Si film as a second film on the entire surface or a part of the first film; forming an insulating film as a third film on the second film; forming an aperture so as to pass through a part of the third film positioned on the second film and not to pass through the second film; etching a part of the substrate on one side of the first film with a solution that does not etch the first film; and etching a part or all of the second film on the other side of the first film with a gas or a solution that does not etch the first film and has an etching rate for the third film lower than an etching rate for the second film, thereby forming a membrane area composed of the first film.

In a preferred specific example for enhancing the measurement accuracy of the device, the membrane area composed of the first film has a thickness of 10 nm or less and 0.3 nm or more. The thickness is more preferably 5 nm or less. The membrane is preferably produced so that the surface area of the membrane area is 1 um$^2$ or less. The shape of the membrane area may be circular or rectangular.

As a specific selection example of the material for the second film, a polysilicon may be mentioned. SiN may be used as a material for the first film. SiN is a good material that can form a stable film.

As a specific selection example of the etching means, a TMAH solution or a KOH solution may be used for etching the substrate or second film. An alkaline substance other than a TMAH solution and a KOH solution may be used.

As another etching method, a xenon fluoride may be used for etching a part of the second film.

Other examples of a material of the first film include at least one selected from HfO$_2$, HfAlO$_x$, ZrAlO$_x$, Ta$_2$O$_5$, SiC, SiCN, a carbon film, and a composite thereof.

Another aspect of the present invention is a membrane device, including: a Si substrate; a first film formed on the substrate and made of at least one selected from SiN, HfO$_2$, HfAlO$_x$, ZrAlO$_x$, Ta$_2$O$_5$, SiC, SiCN, a carbon film, and a composite thereof; a Si film formed on the first film; and a second film formed on the Si film; wherein a first aperture is formed so as to pass through a part of the Si film positioned on the first film and the second film and reach the first film surface, a second aperture is formed so as to pass through a part of the substrate positioned under the first film and reach the first film surface, and at least a part of the first film whose surface is exposed from the first aperture and the second aperture is formed as a membrane area having a thickness of 0.3 nm or more and 10 nm or less.

A further aspect of the present invention is a membrane device, including: a Si substrate; a $SiO_2$ area formed on the substrate; a first film formed on the $SiO_2$ area and made of at least one selected from SiN, $HfO_2$, $HfAlO_x$, $ZrAlO_x$, $Ta_2O_5$, SiC, SiCN, a carbon film, and a composite thereof; a second film formed on the first film; wherein a first aperture is formed in a part of the second film positioned on the first film so as to reach the first film surface, a second aperture is formed so as to pass through a part of the substrate positioned under the first film and reach the $SiO_2$ area surface and the first film surface, and at least a part of the first film whose surface is exposed from the first aperture and the second aperture is formed as a membrane area having a thickness of 0.3 nm or more and 10 nm or less.

The $SiO_2$ area may be formed on the substrate using a LOCOS process or an STI process.

A further aspect of the present invention is a method for producing a membrane device, including: forming a $SiO_2$ area on a Si substrate by using a LOCOS process or an STI process; forming on the Si substrate and the $SiO_2$ area a first insulating film made of at least one selected from SiN, $HfO_2$, $HfAlO_x$, $ZrAlO_x$, $Ta_2O_5$, SiC, SiCN, a carbon film, and a composite thereof; forming a Si film as a second film on a part of the first film; forming an insulating film as a third film on the second film; forming an aperture so as to pass through a part of the third film positioned on the second film and not to pass through the second film; etching a part of the substrate on one side of the first film with a solution that does not etch the first film; etching a part or all of the second film on the other side of the first film with a gas or a solution that does not etch the first film and has an etching rate for the third film lower than an etching rate for the second film, thereby forming a membrane area composed of the first film.

A further aspect of the present invention is an analyzer using the membrane device formed as above. In the analyzer, a through hole is formed in the membrane area, a current value flowing through the through hole is measured during a substance passes through the through hole in an aqueous solution, and based on the current value, a structural feature of the substance is analyzed.

An example of the configuration of the analyzer is an analyzer including, a Si substrate, a first film formed on the substrate and made of at least one selected from SiN, $HfO_2$, $HfAlO_x$, $ZrAlO_x$, $Ta_2O_5$, SiC, SiCN, a carbon film, and a composite thereof, a Si film formed on the first film, and a second film formed on the Si film, wherein a first aperture is formed so as to pass through a part of the Si film positioned on the first film and the second film and reach the first film surface, a second aperture is formed so as to pass through a part of the substrate positioned under the first film and reach the first film surface, at least a part of the first film whose surface is exposed from the first aperture and the second aperture is formed as a membrane area having a thickness of 0.3 nm or more and 10 nm or less, and wherein a through hole is formed in the membrane area, a current value flowing through the through hole is measured during a substance passes through the through hole in an aqueous solution, and based on the current value, a structural feature of the substance is analyzed.

Advantageous Effects of Invention

According to the present application, it is possible to form an inorganic material membrane that is thinner than before.

BRIEF DESCRIPTION OF DRAWINGS

FIG. 1 It is a cross section illustrating an embodiment of Example 1.
FIG. 2 It is a cross section illustrating the embodiment of Example 1.
FIG. 3 It is a cross section illustrating the embodiment of Example 1.
FIG. 4 It is a cross section illustrating the embodiment of Example 1.
FIG. 5 It is a cross section illustrating the embodiment of Example 1.
FIG. 6 It is a cross section illustrating the embodiment of Example 1.
FIG. 7 It is a cross section illustrating the embodiment of Example 1.
FIG. 8 It is a cross section illustrating the embodiment of Example 1.
FIG. 9 It is a graph showing an effect of Example 1.
FIG. 10 It is a cross section illustrating an embodiment of Example 2.
FIG. 11 It is a cross section illustrating the embodiment of Example 2.
FIG. 12 It is a cross section illustrating the embodiment of Example 2.
FIG. 13 It is a cross section illustrating the embodiment of Example 2.
FIG. 14 It is a cross section illustrating the embodiment of Example 2.
FIG. 15 It is a cross section illustrating the embodiment of Example 2.
FIG. 16 It is a cross section illustrating the embodiment of Example 2.
FIG. 17 It is a cross section illustrating the embodiment of Example 2.
FIG. 18 It is a cross section illustrating the embodiment of Example 2.
FIG. 19 It is a cross section illustrating the embodiment of Example 2.
FIG. 20 It is a cross section illustrating an embodiment of Example 3.
FIG. 21 It is a cross section illustrating the embodiment of Example 3.
FIG. 22 It is a cross section illustrating the embodiment of Example 3.
FIG. 23 It is a cross section illustrating the embodiment of Example 3.
FIG. 24 It is a cross section illustrating the embodiment of Example 3.
FIG. 25 It is a cross section illustrating the embodiment of Example 3.
FIG. 26 It is a cross section illustrating the embodiment of Example 3.
FIG. 27 It is a cross section illustrating the embodiment of Example 3.
FIG. 28 It is a cross section illustrating the embodiment of Example 3.
FIG. 29 It is a cross section illustrating the embodiment of Example 3.
FIG. 30 It is a cross section illustrating the embodiment of Example 3.
FIG. 31 It is a cross section illustrating an embodiment of Example 4.
FIG. 32 It is a cross section illustrating the embodiment of Example 4.
FIG. 33 It is a cross section illustrating the embodiment of Example 4.

FIG. 34 It is a cross section illustrating the embodiment of Example 4.

FIG. 35 It is a cross section illustrating the embodiment of Example 4.

FIG. 36 It is a cross section illustrating the embodiment of Example 4.

FIG. 37 It is a cross section illustrating the embodiment of Example 4.

FIG. 38 It is a cross section illustrating the embodiment of Example 4.

FIG. 39 It is a cross section illustrating the embodiment of Example 4.

FIG. 40 It is a cross section illustrating the embodiment of Example 4.

FIG. 41 It is a cross section illustrating the embodiment of Example 4.

FIG. 42 It is a cross section illustrating an embodiment of Example 5.

DESCRIPTION OF EMBODIMENTS

The same sign is given to components having the same function in all the drawings for explaining the embodiments, and the repeated explanation is omitted as much as possible. Hereinunder, the embodiments of the present invention will be described in detail based on the drawings. The structure and materials of a device described in each Example is one example for embodying the concept of the present invention, and are not intended to strictly define the materials and dimensions.

The terms [first], [second], [third], and the like in the Description are added for distinguishing the components, and the terms are not necessarily intended to limit the number or the order. The numerals for distinguishing the components are used for each context, and a number used in one context does not necessarily represent an identical configuration in another context. In addition, a component distinguished by a certain number can also have a function of a component distinguished by another number with no limitation.

The position, size, shape, range, and the like of each component shown in the drawings, etc. sometimes do not represent the actual position, size, shape, range, and the like for the sake of easy understanding of the invention. Accordingly, the present invention is not necessarily limited to the position, size, shape, range, and the like disclosed in the drawings, etc.

Example 1

Examples of the present invention will be described below with reference to FIG. 1 to FIG. 9.

(FIG. 1) A SiN film 101 is formed on a Si substrate 100. The thickness of the Si substrate is, for example, 725 um. The thickness of the SiN film 101 is, for example, 3 nm. As the film forming method, for example, a CVD (chemical vapor deposition) method is used. Aside from the CVD method, the Si substrate may be directly subjected to thermal nitration. In this case, for example, under an $NH_3$ atmosphere, annealing at 1000° C. or higher is performed for approximately 1 minute, whereby a high quality SiN film of 1 nm to 2 nm can be formed on the Si substrate. When thermal nitration is used, SiN having a thickness of 0.3 nm can even be formed by controlling the temperature and the time. Then, a Si film 102 is formed on the SiN film 101. As the film forming method, for example, a CVD method is used. The thickness of the Si film is, for example, 150 nm.

As the Si film, for example, non-doped poly-Si is formed into a film. Then, a SiN film 103 is formed on the Si film 102. As the film forming method, for example, a CVD method is used. The thickness of the SiN film 103 is, for example, 100 nm. Then, a SiN film 104 is formed on the back surface of the Si substrate. As the film forming method, for example, a CVD method is used. The thickness of the SiN film 104 is, for example, 200 nm.

(FIG. 2) A resist 105 is applied on the SiN film 103, and a part thereof is exposed to light to open the part using a lithography technique. The exposure area is, for example, $100 \times 100$ $nm^2$.

(FIG. 3) A part of the SiN film 103 is etched by dry etching using the resist as a mask. Then, the resist is removed by an asher.

(FIG. 4) A resist 106 is applied on the SiN film 104, a part thereof is exposed to light to open the part using a lithography technique. The exposure area is, for example, $1038 \times 1038$ $um^2$.

(FIG. 5) A part of the SiN film 104 is etched by dry etching using the resist as a mask. Then, the resist is removed by an asher.

(FIG. 6) An organic protection film is applied on the surface, and then a part of the Si substrate 100 is etched with a KOH (potassium hydroxide) aqueous solution, a TMAH (tetramethylammonium hydroxide) aqueous solution, or another alkaline solution which does not etch the film 101. After etching, the organic protection film on the surface is removed using acetone or oxygen asking. As the organic protection film, for example, ProTEK® B3 primer and ProTEK® B3 from Brewer Science, Inc. or the like are used.

(FIG. 7) A part of the Si film 102 is etched using the SiN film 103 as a mask with a KOH aqueous solution, a TMAH aqueous solution, or another alkaline solution which does not etch the SiN film 101. For example, in the case of using a KOH aqueous solution, by performing etching at a concentration of 25 wt % at room temperature for approximately 16 minutes, the Si film 102 having a thickness of 150 nm is etched, and an extremely small membrane area composed only of the SiN film 101 (1 um×1 um or smaller) can be formed.

Since the thin film membrane area is small and the KOH aqueous solution or TMAH aqueous solution does not etch SiN, a very thin membrane area can be formed.

Through the above process, a thin film membrane area composed only of the SiN film 101 can be formed.

FIG. 8 shows a configuration in which a device formed using the above process is set up to evaluate the device. That is, the opposite sides of the membrane are in contact with a KCl (potassium chloride) aqueous solution 201, and Ag/AgCl electrodes 202 and 203 are immersed in the respective chambers and connected to a voltage source and an ammeter. 901 designates an o-ring for sealing the chambers on the opposite sides of the membrane.

FIG. 9 shows the current value between the electrodes 202 and 203 when a voltage of 0.1 V is applied in the state of FIG. 8. In FIG. 9, the vertical axis shows the current value (A) between the electrodes 202 and 203 when 0.1 V is applied, and the horizontal axis shows the thickness (nm) of the SiN film 101 accumulated during the formation of the device. The points expressed by a square in the graph represent data in the case where the devices are produced by the production method described in NPL 1 (data in the case where the film 102 is of $SiO_2$ and an HF aqueous solution is used for etching 102). On the other hand, the points expressed by a diamond shape represent data in the case where the devices are produced by the production method of Example 1 (data in the case where the film 102 is of Si and a KOH aqueous solution is used for etching 102). In the graph, a current value of 10 pA or more means defects being present in the membrane from the beginning (pinholes and tears being present from the beginning). In contrast, when a current value is 10 pA or less, no initial defect is present in the membrane. In FIG. 9, in the case where the device is produced by the production method described in NPL 1, there is an initial defect when the accumulated thickness of the membrane is 7 nm or less, and a current value that leaks from the defect to flow is observed. That is, a SiN membrane having a thickness of 7 nm or less can not be formed by the production method of NPL 1. In addition, also by the production method of NPL 2 in which a thin film membrane is studied, it is reported that the film thickness of the SiN membrane that could be formed was 5 to 8 nm, and a membrane thinner than 5 nm could not be formed. In addition, in any other report, there is no example of the case where a membrane thinner than 5 nm could be formed with SiN.

On the other hand, in the case of the production method of the present invention, as shown in FIG. 9, a SiN membrane with a thickness less than 5 nm and having no initial defect could be formed. As shown in FIG. 9, to the extent that has been heretofore confirmed, even in SiN membranes having a thickness of 3.18 nm as measured by ellipsometry, it was confirmed that a membrane with no initial defect could be formed.

Other characteristics of the present production method than capability of forming a thin film of a membrane will be described below. A membrane produced by the production method is excellent in film thickness uniformity of the membrane in a wafer surface.

In the devices used in the experimental results shown in FIG. 9, the SiN film 101 was formed by a CVD method on a Si wafer of 8 inches, and when 25 points in the surface of the SiN film 101 were measured by an ellipsometer immediately after forming the film, the thickness was 3.18 nm on average, 3.35 nm at a maximum, and 3.10 nm at a minimum, and had a very small variation of 0.25 nm in the surface. Since a film to be a membrane is formed just above the Si substrate surface which is flat in the order of atomic layer, such a small variation in thickness can be achieved. Furthermore, since subsequent etching of SiN with a TMAH aqueous solution or a KOH aqueous solution is not required, the film thickness of the membrane during the film formation is substantially not changed until the membrane is formed. Accordingly, the film thickness uniformity of the membrane is very high in a wafer surface, and in the case of mass production of the device, many acceptable products which conform to a desired thickness specification can be obtained.

Also when a membrane having a thickness of 5 nm or larger is formed, by using this process, as compared with the case where a membrane is formed using the processes in the conventionally reported examples (NPL 1, NPL 2), the film thickness uniformity in a wafer surface and the yield are enhanced. In the process of NPL 1, as described in Background Art, since the SiN membrane is exposed to an HF aqueous solution, the SiN membrane is damaged, lowering the production yield. In addition, an HF aqueous solution etches a SiN membrane, and therefore, due to the variation in the etching level, there occurs a variation in the film thickness of the final membrane produced. In the process of NPL 2, a thin film membrane is formed also using dry etching, in addition to etching with a HF aqueous solution. Particularly in dry etching, there occurs a large variation in etching rate from one process to another, and from one wafer to another. In addition, the variation in etching rate is large also in a wafer surface. Thus, there occurs a large variation in film thickness of the finished membrane from one process to another, from one wafer to another, and in one wafer surface. Needless to say, both of etching with an HF aqueous solution and dry etching damage the membrane, and therefore considerably lower the production yield.

In the process of the present invention, as described above, the film thickness uniformity of the membrane in a wafer surface is very high, and since the membrane is not damaged, the production yield is also very high.

As described above, also when a membrane having a film thickness of, for example, 5 to 10 nm or larger is formed, as compared with the case where a membrane is formed using the conventionally reported processes (NPL 1, NPL 2), in the case of using the process of the present invention, the film thickness uniformity of the membrane is higher and the production yield is also higher.

For example, presence or absence of a specific deletion or modification in a part of DNA can be determined by using a membrane of a 10 nm thickness having a nanopore formed therein and allowing the DNA to pass through the nanopore in an ionic aqueous solution, and then measuring the variation in conductance of the current flowing through the nanopore. Not only specific deletion or modification in a part of DNA, but also structural features of an arbitrary biological substance can be grasped in an accuracy degree of space resolution of approximately 10 nm or lower by using a membrane of a 10 nm thickness having a nanopore formed therein.

The Si film 102 may be an amorphous Si film, aside from a poly-Si film.

Etching of the Si film 102 may be performed with a xenon fluoride, aside from a KOH aqueous solution, a TMAH aqueous solution, or another alkaline solution. The etching rate with a xenon fluoride for SiN is 1000 times higher than the etching rate therewith for Si. For this reason, if the Si film 102 is etched 150 nm and the etching is stopped at the time when the SiN film 101 under the Si film is exposed as in this Example, the SiN film 101 is not scratched.

The film 103 may be made of any material aside from SiN, as long as it has a sufficient difference in etching rate from Si such that the film is not scratched or is difficult to scratch when the Si film 102 is etched. For example, a $SiO_2$ film may be used with no problem because, if a TMAH aqueous solution, a KOH aqueous solution, or a xenon fluoride is used in etching the Si film 102, the etching rate is significantly lower for $SiO_2$ than for Si and the $SiO_2$ film is never lost.

Similarly, the film 104 may be made of any material aside from SiN, as long as it has a sufficient difference in etching rate from Si such that the film is not scratched or is difficult to scratch when the Si substrate 100 is etched.

The film 101 may be any film aside from a SiN film, as long as it is made of a material that is not etched with a TMAH aqueous solution, a KOH aqueous solution, or another alkaline solution when such a TMAH aqueous solution, a KOH aqueous solution, or another alkaline solution is used as an etching solution for etching the Si substrate 100 and the Si film 102. Examples thereof include $HfO_2$, $HfAlO_x$, $ZrAlO_x$, $Ta_2O_5$, SiC, SiCN, a carbon film, and a composite thereof. Also in a membrane made of these materials, a membrane thinner than 5 nm can be formed by using the present production method.

Example 2

In FIG. 10 to FIG. 19, Example 2 in which the area formed by the membrane 101 film can be made narrower will be shown. As described above, the narrower the membrane area, the smaller thickness the membrane can be formed into and the higher the yield is.

(FIG. 10) The SiN film 101 is formed on the Si substrate 100. The thickness of the Si substrate is, for example, 725 um. The thickness of the SiN film 101 is, for example, 3 nm. As the method of forming the film, for example, a CVD (chemical vapor deposition) method is used. Aside from the CVD method, the Si substrate may be directly subjected to thermal nitration. In this case, for example, under an $NH_3$ atmosphere, annealing at 1000° C. or higher is performed for approximately 1 minute, whereby a high quality SiN film of 1 nm to 2 nm can be formed on the Si substrate. Then, the Si film 102 is formed on the SiN film 101. As the film forming method, for example, a CVD method is used. The thickness of the Si film is, for example, 150 nm. As the Si film, for example, non-doped poly-Si is formed into a film. Then, the SiN film 104 is formed on the back surface of the Si substrate. As the film forming method, for example, a CVD method is used. The thickness of the SiN film 104 is, for example, 200 nm.

(FIG. 11) The resist 105 is applied on a part of the film 102, and a part thereof is exposed to light to form a shape as shown in FIG. 11 using a lithography technique. The surface area of 105 viewed from above is, for example, 600 nm×600 nm. Then, boron is implanted in the film 102 by ion-implantation. The conditions of the implantation are, for example, an energy of 3 keV and a dose of $2 \times 10^{15}$ cm$^{-2}$. Then, the resist is removed by an asher.

(FIG. 12) Then, boron is activated and dispersed by annealing at 950° C. for 120 seconds under N2 atmosphere to produce a B-doped poly-Si layer 110. The remaining non-doped poly-Si area after annealing is about 100 to 200 nm$^2$.

(FIG. 13) Then, the SiN film 103 is formed. As the film forming method, for example, a CVD method is used. The thickness of the SiN film 103 is, for example, 100 nm.

(FIG. 14) The resist 105 is applied on the SiN film 103, and a part thereof is exposed to light to open the part using a lithography technique. The exposure area is, for example, 100×100 nm$^2$.

(FIG. 15) A part of the SiN film 103 is etched by dry etching using the resist as a mask. Then, the resist is removed by an asher.

(FIG. 16) The resist 106 is applied on the SiN film 104, a part thereof is exposed to light to open the part using a lithography technique. The exposure area is, for example, 1038×1038 um$^2$.

(FIG. 17) A part of the SiN film 104 is etched by dry etching using the resist as a mask. Then, the resist is removed by an asher.

(FIG. 18) An organic protection film is applied on the surface, and then a part of the Si substrate 100 is etched using a KOH aqueous solution, a TMAH (tetramethylammonium hydroxide) aqueous solution, or another alkaline solution which does not etch the film 101. After etching, the organic protection film on the surface is removed using acetone or oxygen asking. As the organic protection film, for example, ProTEK® B3 primer and ProTEK® B3 from Brewer Science, Inc. or the like is used.

(FIG. 19) The Si film 102 is etched with a KOH aqueous solution which does not etch the film 101 using the SiN film 103 as a mask. In the case of using a KOH aqueous solution, by performing etching at a concentration of 25 wt % at room temperature for approximately 16 minutes, the Si film 102 of a thickness of 150 nm is etched, and an extremely small membrane area composed only of the SiN film 101 can be formed. In this case, the etching rate for the boron-doped poly-Si area 110 with a KOH aqueous solution is significantly lower than for the non-doped poly-Si area 102. Accordingly, progress of etching toward the in-plane direction (lateral direction) of the film 110 can be suppressed. Thus, a narrower membrane area can be formed than in Example 1, and as a result, it becomes possible to form a thinner membrane and to enhance the yield of obtaining acceptable membrane products.

The Si film 102 may be an amorphous Si film, aside from a poly-Si film.

The film 103 may be made of any material aside from SiN, as long as it has a sufficient difference in etching rate from Si such that the film is not scratched or is difficult to scratch in etching the Si film 102. For example, a $SiO_2$ film may be used with no problem because, if a KOH aqueous solution is used in etching the Si film 102, the etching rate for $SiO_2$ is significantly lower than for Si and the $SiO_2$ film is never lost.

The film 104 may be made of any material aside from SiN, as long as it has a sufficient difference in etching rate from Si such that the film is not scratched or is difficult to scratch in etching the Si substrate 100.

The film 101 may be any film aside from a SiN film, as long as it is made of a material that is not etched with a KOH aqueous solution, when such a KOH aqueous solution is used as an etching solution for etching the Si substrate 100 and the Si film 102. Examples thereof include $HfO_2$, $HfAlO_x$, $ZrAlO_x$, $Ta_2O_5$, SiC, SiCN, a carbon film, and a composite thereof. Also in a membrane made of these materials, a membrane thinner than 5 nm can be formed by using the present production method.

Example 3

With reference to FIG. 20 to FIG. 30, a production method of Example 3 in which there remains no Si film in an upper portion of a membrane (Si film on the opposite side of the membrane film from the Si substrate) at the completion of a device is shown. When an object to be measured such as DNA is electrically measured after forming a nanopore in the membrane, if Si film is present in the vicinity of a nanopore, as compared with the case of no Si film, an electric noise due to an external electromagnetic field is more likely to be detected. For this reason, in order to enhance the measurement accuracy, it is effective to remove the Si film in an upper portion of the membrane (Si film on the opposite side of the membrane film from the Si substrate) as much as possible.

(FIG. 20) A $SiO_2$ film 300 is formed on the Si substrate 100 using a LOCOS process (local oxidation of silicon) which is an element isolation process well known as a semiconductor process. The thickness of the Si substrate is, for example, 725 um. The thickness of the $SiO_2$ film is, for example, 400 nm. An active area with no $SiO_2$ film (an area where the Si substrate is exposed) is, for example, 500 nm×500 nm. A smaller area is preferred since the area will determine the area of a membrane 301 later. (The smaller the area is, the thinner membrane can be formed and the more the yield is enhanced.) Then, the SiN film 104 is formed on the back surface of the Si substrate 100. The thickness of 104 is, for example, 200 nm. As the film forming method, for example, a CVD method is used.

(FIG. 21) Then, the SiN film 301 of, for example, 3 nm is formed. As the film forming method, for example, a CVD (chemical vapor deposition) method is used. Aside from the CVD method, the Si substrate may be directly subjected to thermal nitration. In this case, for example, under an NH$_3$ atmosphere, annealing at 1000° C. or higher is performed for approximately 1 minute, whereby a high quality SiN film of 1 nm to 2 nm can be formed on the Si substrate. Then, a Si film 302 is formed on the SiN film 301. As the film forming method, for example, a CVD method is used. The thickness of the Si film is, for example, 150 nm. As the Si film, for example, non-doped poly-Si is formed into a film.

(FIG. 22) A resist 310 is applied and exposed to light to form a pattern as shown in FIG. 22 using a lithography technique. In this case, the ends of the pattern are made to exist above the SiO$_2$ film 300. By this configuration, in dry etching in the next step, even if the film 301 to be a membrane is etched, the thick SiO$_2$ film 300 is present under the film 301. Therefore, as long as the film 300 is not largely scratched, there arises no problem in forming the membrane. The area of 310 viewed from above is, for example, 1 um×1 um.

(FIG. 23) The film 302 is etched by dry etching using the resist as a mask. Then, the resist is removed by asking.

(FIG. 24) Then, a SiN film 303 is formed. The film thickness is, for example, 100 nm. As the film forming method, for example, a CVD method is used.

(FIG. 25) A resist 304 is applied and a part thereof is exposed to light to form a pattern, as shown in FIG. 25, by a lithography technique. The opening area viewed from above is, for example, 700 nm×700 nm.

(FIG. 26) The SiN film 303 is etched by dry etching using the resist as a mask. Then, the resist is removed by an asher.

(FIG. 27) The resist 106 is applied on the back surface of the Si substrate 100, and as shown in FIG. 27, a part thereof is exposed to light to form a pattern by a lithography technique. The exposure area is, for example, 1038×1038 um$^2$.

(FIG. 28) A part of the SiN film 104 is etched by dry etching using the resist as a mask. Then, the resist is removed by an asher.

(FIG. 29) An organic protection film is applied on the surface, and then a part of the Si substrate 100 is etched with a KOH aqueous solution, a TMAH (tetramethylammonium hydroxide) aqueous solution, or another alkaline solution which does not etch the film 301. After etching, the organic protection film on the surface is removed with acetone or oxygen asking. As the organic protection film, for example, ProTEK® B3 primer and ProTEK® B3 from Brewer Science, Inc., or the like is used.

(FIG. 30) Using the SiN film 303 as a mask, the Si film 302 is etched with a KOH aqueous solution, a TMAH aqueous solution, or another alkaline solution which does not etch the film 301. For example, when using a KOH aqueous solution, by performing etching at a concentration of 25 wt % at room temperature for approximately 30 minutes, all of the Si film 302 of a thickness of 150 nm is etched and an extremely small membrane area (surface area of 500 nm×500 nm in this Example) composed only of the SiN film 301 can be formed.

According to the production method, there remains no Si film in an upper portion of the membrane (Si film on the opposite side of the membrane film from the Si substrate). For this reason, after forming a nanopore in the membrane, measurement of the ionic current passing through the nanopore is less liable to be affected by a noise due to an external electromagnetic field. Accordingly, a more accurate measurement can be achieved. The Si film 302 may be an amorphous Si film, aside from the poly-Si film.

The film 303 may be made of any material aside from SiN, as long as it has a sufficient difference in etching rate from Si such that the film is not scratched or is difficult to scratch in etching the Si film 302. For example, a SiO$_2$ film may be used with no problem because, if a TMAH aqueous solution or a KOH aqueous solution is used in etching the Si film 302, the etching rate for SiO$_2$ is significantly lower than for Si and the SiO$_2$ film is never lost.

Similarly, the film 104 may be made of any material aside from SiN, as long as it has a sufficient difference in etching rate from Si such that the film is not scratched or is difficult to scratch in etching the Si substrate 100.

The film 301 may be any film aside from a SiN film, as long as it is made of a material that is not etched with a TMAH aqueous solution, a KOH aqueous solution, or another alkaline solution, when such a TMAH aqueous solution, a KOH aqueous solution, or another alkaline solution is used as an etching solution for etching the Si substrate 100 and the Si film 302. Examples thereof include HfO$_2$, HfAlO$_x$, ZrAlO$_x$, Ta$_2$O$_5$, SiC, SiCN, a carbon film, and a composite thereof. Also in a membrane made of these materials, a membrane thinner than 5 nm can be formed by using the present production method.

Example 4

With reference to FIG. 31 to FIG. 41, as in Example 3, a production method of Example 4 in which there remains no Si film in an upper portion of a membrane (Si film on the opposite side of the membrane film from the Si substrate) at the completion of a device is shown. When an object to be measured such as DNA is electrically measured after forming a nanopore in the membrane, if the Si film is present in the vicinity of the nanopore, as compared with the case of no Si film, an electric noise due to an external electromagnetic field is more likely to be detected. For this reason, in order to enhance the measurement accuracy, it is effective to remove Si film in an upper portion of the membrane (Si film on the opposite side of the membrane film from the Si substrate) as much as possible.

(FIG. 31) A SiO$_2$ film 400 is formed on the Si substrate 100 using an STI process (shallow trench isolation) which is an element isolation process well known as a semiconductor process. The thickness of the Si substrate is, for example, 725 um. The thickness of the SiO$_2$ film is, for example, 400 nm. An active area with no SiO$_2$ film (an area where the Si substrate is exposed) is, for example, 100 nm×100 nm. A smaller area is preferred since the area will determine the area of the membrane 301 later. (The smaller the area is, the thinner membrane can be formed and the more the yield is enhanced.) Incidentally, the STI process has more advantage as compared with the LOCOS process in that the area can be controlled smaller. Then, the SiN film 104 is formed on the back surface of the Si substrate 100. The thickness of 104 is, for example, 200 nm. As the film forming method, for example, a CVD method is used.

(FIG. 32) Then, a SiN film 401 of, for example, 3 nm is formed. As the film forming method, for example, a CVD (chemical vapor deposition) method is used. Aside from the CVD method, the Si substrate may be directly subjected to thermal nitration. In this case, for example, under an NH$_3$ atmosphere, annealing at 1000° C. or higher is performed for approximately 1 minute, whereby a high quality SiN film of 1 nm to 2 nm can be formed on the Si substrate. Then, a Si film 402 is formed on the SiN film 401. As the film forming method, for example, a CVD method is used. The thickness of the Si film is, for example, 150 nm. As the Si film, for example, non-doped poly-Si is formed into a film.

(FIG. 33) A resist 410 is applied and exposed to light to form a pattern as shown in FIG. 33 using a lithography technique. In this case, the ends of the pattern are made to exist above the SiO$_2$ film 400. By this configuration, in dry etching in the next step, even if the film 401 to be a membrane is etched, the thick SiO$_2$ film 400 is present under the film 401. Therefore, as long as the film 400 is not largely scratched, there arises no problem in forming the membrane. The area of 410 viewed from above is, for example, 500 nm×500 nm.

(FIG. 34) The film 402 is etched by dry etching using the resist as a mask. Then the resist is removed by asking.

(FIG. 35) Then, a SiN film 403 is formed. The film thickness is, for example, 100 nm. As the film forming method, for example, a CVD method is used.

(FIG. 36) A resist 404 is applied and a part thereof is exposed to light to form a pattern, as shown in FIG. 36, by a lithography technique. The opening area viewed from above is, for example, 300 nm×300 nm.

(FIG. 37) The SiN film 403 is etched by dry etching using the resist as a mask. Then, the resist is removed by an asher.

(FIG. 38) The resist 106 is applied on the back surface of the Si substrate 100, and as shown in FIG. 38, a part thereof is exposed to light to form a pattern by a lithography technique. The exposure area is, for example, 1038×1038 um$^2$.

(FIG. 39) A part of the SiN film 104 is etched by dry etching using the resist as a mask. Then, the resist is removed by an asher.

(FIG. 40) An organic protection film is applied on the surface, and then a part of the Si substrate 100 is etched with a KOH aqueous solution, a TMAH (tetramethylammonium hydroxide) aqueous solution, or another alkaline solution which does not etch the film 401. After etching, the organic protection film on the surface is removed with acetone or oxygen asking. As the organic protection film, for example, ProTEK® B3 primer and ProTEK® B3 from Brewer Science, Inc., or the like is used.

(FIG. 41) Using the SiN film 403 as a mask, the Si film 402 is etched with a KOH aqueous solution, a TMAH aqueous solution, or another alkaline solution which does not etch the film 401. For example, in the case of using a KOH aqueous solution, by performing etching at a concentration of 25 wt % at room temperature for approximately 20 minutes, all the Si film 402 with a thickness of 150 nm is etched, and an extremely small membrane area (a surface area of 100 nm×100 nm in this Example) composed only of the SiN film 401 can be formed.

According to the production method, there remains no Si film in an upper portion of the membrane (Si film on the opposite side of the membrane film from the Si substrate). For this reason, after forming a nanopore in the membrane, measurement of the ionic current passing through the nanopore is less liable to be affected by a noise due to an external electromagnetic field. Accordingly, a more accurate measurement can be achieved. In addition, by using the STI process, as compared with the case using the LOCOS process, it is possible to form a narrower membrane area of the 401 film, and as a result, it becomes possible to form a thinner membrane and enhance the yield of obtaining acceptable membrane products. The Si film 402 may be an amorphous Si film, aside from the poly-Si film.

The film 403 may be made of any material aside from SiN, as long as it has a sufficient difference in etching rate from Si such that the film is not scratched or is difficult to scratch in etching the Si film 402. For example, a SiO$_2$ film may be used with no problem because, if a TMAH aqueous solution or a KOH aqueous solution is used in etching the Si film 402, the etching rate for SiO$_2$ is significantly lower than for Si and the SiO$_2$ film is never lost.

Similarly, the film 104 may be made of any material aside from SiN, as long as it has a sufficient difference in etching rate from Si such that the film is not scratched or is difficult to scratch in etching the Si substrate 100.

The film 401 may be any film aside from a SiN film, as long as it is made of a material that is not etched with a TMAH aqueous solution, a KOH aqueous solution, or another alkaline solution, when such a TMAH aqueous solution, a KOH aqueous solution, or another alkaline solution is used as an etching solution for etching the Si substrate 100 and the Si film 402. Examples thereof include HfO$_2$, HfAlO$_2$, ZrAlO$_2$, Ta$_2$O$_5$, SiC, SiCN, a carbon film, and a composite thereof. Also in a membrane made of these materials, a membrane thinner than 5 nm can be formed by using the present production method.

Example 5

In FIG. 42, with a device formed in Example 1 to 4, a method for measuring an object to be measured in an aqueous solution is shown. Although DNA is exemplified in the Example, the method is useful for structure determination of a variety of substances other than DNA. The opposite sides of the membrane are in contact with the KCl aqueous solution 201, and the Ag/AgCl electrodes 202 and 203 are immersed in the respective chambers and are connected to a voltage source and an ammeter. 901 designate an o-ring for sealing the chambers on the opposite sides of the membrane. The controls of the ammeter and the voltage source are performed by a PC for control and analysis. The input and output of the KCl aqueous solution are performed through inlets 1001 and 1003 and outlets 1002 and 1004.

First, formation of a nanopore in a membrane, which are formed in Examples 1 to 4, is performed in a KCl aqueous solution. According to the method of NPL 1, a pulse voltage substantially equal to the dielectric breakdown voltage of the film 101 is applied to the membrane to form a nanopore by dielectric breakdown. Then, DNA to be measured is injected, for example, from the inlet 1001. Then, a voltage of 0.1 V is applied to the electrode 202 and a voltage of 0 V is applied to the electrode 201 to cause the DNA to undergo phoresis toward the nanopore and to pass through the nanopore.

The ionic current value flowing through the nanopore during the DNA undergoes phoresis in the nanopore is measured by the ammeter and the measurement value is recorded by the PC. Then, by analyzing the time-dependent variation of the current value measured, it is possible to acquire information on the structure of the DNA and identify the base sequence of the DNA.

The present invention is not limited to the embodiments described above, and encompasses a variety of modified examples. For example, a part of a configuration in one Example may be replaced with a configuration in any other Example, and a configuration in one Example may be added to a configuration in any other Example. In addition, with respect to a part of a configuration of each Example, a configuration in any other Example may be added, deleted, or replaced.

INDUSTRIAL AVAILABILITY

The present invention can be used in a detection technique for acquisition of information of DNA, and the like.

REFERENCE SIGNS LIST

100: SiSubstrate
101: Film (SiN film, etc.)
102: Film (Si film)
103: Film (SiN film, etc.)
104: Film (SiN film, etc.)
105: Film (resist)
106: Film (resist)
110: Film (boron-doped Si film)
201: Ionic aqueous solution (KCl aqueous solution)
202: Electrode (Ag/AgCl electrode)
203: Electrode (Ag/AgCl electrode)
300: Film ($SiO_2$ film)
301: Film (SiN film, etc.)
302: Film (Si film)
303: Film (SiN film, etc.)
304: Film (resist)
310: Film (resist)
400: Film ($SiO_2$ film)
401: Film (SiN film, etc.)
402: Film (Si film)
403: Film (SiN film, etc.)
404: Film (resist)
410: Film (resist)
901: O-ring
1001: Inlet for solution
1002: Outlet for solution
1003: Inlet for solution
1004: Outlet for solution

The invention claimed is:

1. A method for producing a membrane device, comprising:
   forming an insulating film as a first film on a Si substrate as a substrate;
   forming a Si film as a second film on the entire surface or a part of the first film;
   forming an insulating film as a third film on the second film;
   forming an aperture so as to pass through a part of the third film positioned on the second film and not to pass through the second film;
   etching a part of the substrate on one side of the first film with a solution that does not etch the first film; and
   etching a part or all of the second film on the other side of the first film with a gas or a solution that does not etch the first film and has an etching rate for the third film lower than an etching rate for the second film, thereby forming a membrane area composed of the first film.

2. The method for producing a membrane device according to claim 1, wherein the membrane area composed of the first film has a thickness of 10 nm or less and 0.3 nm or more.

3. The method for producing a membrane device according to claim 1, wherein the membrane area composed of the first film has a thickness less than 5 nm and 0.3 nm or more.

4. The method for producing a membrane device according to claim 1, wherein at least one selected from SiN, $HfO_2$, $HfAlO_x$, $ZrAlO_x$, $Ta_2O_5$, SiC, SiCN, a carbon film, and a composite thereof is used as a material of the first film.

5. The method for producing a membrane device according to claim 1, wherein the membrane device is produced so that the membrane area composed of the first film has a surface area of 1 um2 or less.

6. The method for producing a membrane device according to claim 5, wherein, when the substrate or the second film is etched, the etching is performed with a TMAH solution, a KOH solution, or another alkaline substance.

7. The method for producing a membrane device according to claim 5, wherein, when the part of the second film is etched, the etching is performed with a xenon fluoride.

8. A membrane device, comprising:
   a Si substrate;
   a first film formed on the substrate and made of at least one selected from SiN, $HfO_2$, $HfAlO_x$, $ZrAlO_x$, $Ta_2O_5$, SiC, SiCN, a carbon film and a composite thereof;
   a Si film formed on the first film; and
   a second film formed on the Si film,
   wherein:
   a first aperture is formed so as to pass through a part of the Si film positioned on the first film and the second film to reach the first film surface,
   a second aperture is formed so as to pass through a part of the substrate positioned under the first film to reach the first film surface, and
   at least a part of the first film whose surface is exposed from the first aperture and the second aperture is formed as a membrane area having a thickness of 0.3 nm or more and less than 10 nm.

9. The membrane device according to claim 8, wherein the membrane area has the thickness which is less than 5 nm.

10. The membrane device according to claim 8, wherein the membrane area has a surface area of 1 $\mu m^2$ or smaller.

11. The membrane device according to claim 8, wherein B is implanted in at least a part of the Si film formed on the first film.

12. A method for producing a membrane device, comprising:
   forming a SiO2 area on a Si substrate using a LOCOS process or an STI process;
   forming, on the Si substrate and the SiO2 area, a first insulating film made of at least one selected from SiN, $HfO_2$, $HfAlO_x$, $ZrAlO_x$, $Ta_2O_5$, SiC, SiCN, a carbon film, and a composite thereof;
   forming a Si film as a second film on a part of the first film;
   forming an insulating film as a third film on the second film;
   forming an aperture so as to pass through a part of the third film positioned on the second film and not to pass through the second film;
   etching a part of the substrate on one side of the first film with a solution that does not etch the first film; and
   etching a part or all of the second film on the other side of the first film with a gas or a solution that does not etch the first film and that has an etching rate for the third film lower than an etching rate for the second film, thereby forming a membrane area composed of the first film.

13. The method for producing a membrane device according to claim 12, wherein the membrane area composed of the first film has a thickness of 10 nm or less and 0.3 nm or more.

14. The method for forming a membrane device according to claim 12, wherein, when the substrate or the second film is etched, the etching is performed with a TMAH solution, a KOH solution, or another alkaline substance.

15. The method for forming a membrane device according to claim 12, wherein, when the part of the second film is etched, the etching is performed with a xenon fluoride.

* * * * *